United States Patent [19]

Takeuchi et al.

[11] Patent Number: 5,258,537
[45] Date of Patent: Nov. 2, 1993

[54] METHOD FOR PREPARING ORGANOMONOCHLOROSILANE

[75] Inventors: Masaki Takeuchi; Toshinobu Ishihara; Tohru Kubota; Mikio Endo, all of Niigata, Japan

[73] Assignee: Shin-Etsu Chemical Co., Ltd., Tokyo, Japan

[21] Appl. No.: 16,289

[22] Filed: Feb. 11, 1993

[30] Foreign Application Priority Data

Feb. 18, 1992 [JP] Japan .................. 4-031085

[51] Int. Cl.$^5$ .................................. C07F 7/08
[52] U.S. Cl. ........................................ 556/467
[58] Field of Search .......................... 556/467

[56] References Cited

U.S. PATENT DOCUMENTS

| | | | |
|---|---|---|---|
| 2,500,761 | 3/1950 | Lewis | 556/467 |
| 2,615,034 | 10/1952 | Hyde | 556/467 |
| 3,689,519 | 9/1972 | Lefort | 556/467 X |
| 4,168,277 | 9/1979 | Mitschke et al. | 260/501.5 |
| 4,417,067 | 11/1983 | Kötzsch et al. | 556/467 |
| 4,780,556 | 10/1988 | Hata et al. | 556/467 |

FOREIGN PATENT DOCUMENTS

0461597 12/1991 European Pat. Off.
967592 6/1948 France.

*Primary Examiner*—Paul F. Shaver
*Attorney, Agent, or Firm*—Sughrue, Mion, Zinn, Macpeak & Seas

[57] ABSTRACT

An organodisiloxane represented by the general formula: $R^1R^2R^3SiOSiR^4R^5R^6$ is reacted with thionyl chloride in the presence of an ammonium salt represented by the general formula: $R^7R^8R^9R^{10}NX$ wherein $R^1$ to $R^5$ and $R^{10}$ may be the same or different and each represents a monovalent hydrocarbon group or a hydrogen atom; $R^7$ to $R^9$ may be the same or different and each represents a monovalent hydrocarbon group; and X represents a monovalent anion. Thus, organomonochlorosilanes represented by $R^1R^2R^3SiCl$ and $R^4R^5R^6SiCl$ can be obtained.

6 Claims, No Drawings

METHOD FOR PREPARING ORGANOMONOCHLOROSILANE

BACKGROUND OF THE INVENTION

The present invention relates to a novel method for preparing an organomonochlorosilane which serves as an intermediate material for the preparation of silylating agents or other various kinds of organosilicon compounds.

As methods for preparing organomonochlorosilanes represented by the formula: $R^1R^2R^3SiCl$ starting from organodisiloxanes, there have conventionally been known, for instance, a method disclosed in Japanese Patent Provisional Publication No. 52-65226 in which an organodisiloxane is reacted with a dialkyldichlorosilane in the presence of hexamethylphosphoric acid triamide as a catalyst.

This method which makes use of dialkyldichlorosilanes accompanies formation of polysiloxanes as by-products. The polysiloxane is quite viscous and accordingly, when isolating, by distillation, the organomonochlorosilane as the subject product from the reaction solution, it is needed to extremely raise the temperature of the reaction vessel for distillation. Moreover, a viscous oily product remains in the reaction vessel after the distillation. This makes the post-treatment of the reaction vessel quite difficult. In addition, hexamethylphosphoric acid triamide used as the catalyst is one of carcinogens and, therefore, handling of the starting materials and treatment of waste liquor must be carefully carried out.

SUMMARY OF THE INVENTION

The object of the present invention is generally to solve the foregoing problems associated with the conventional methods for preparing organomonochlorosilanes and more specifically to a method for preparing an organomonochlorosilane in which the purification of the subject product can be performed without extremely raising the temperature of a reaction vessel, which makes the handling of reagents, products and waste liquor easy and highly safe and which makes the post-treatment of the reaction vessel easy.

The method for preparing organomonochlorosilane according to the present invention comprises the step of reacting an organodisiloxane represented by the general formula: $R^1R^2R^3SiOSiR^4R^5R^6$ with thionyl chloride in the presence of an ammonium salt represented by the general formula: $R^7R^8R^9R^{10}NX$. In the foregoing general formulas, $R^1$ to $R^6$ and $R^{10}$ may be the same or different and each represents a monovalent hydrocarbon group or a hydrogen atom; $R^7$ to $R^9$ may be the same or different and each represents a monovalent hydrocarbon group; and X represents a monovalent anion.

According to the method of the present invention, it is not necessary to use hexamethylphosphoric acid triamide. The method does not accompany the formation of any viscous oily product as a by-product which results in a substantial increase of the temperature for the distillation of the reaction solution. The method accompanies the generation of sulfur dioxide gas as a by-product, but the by-product is a gaseous substance capable of being easily handled. The method does not require the use of other dangerous reagents and does not accompany the formation of any dangerous product.

As has been described above, the method does not accompany the formation of a viscous oily substance. This permits substantial reduction of the distillation temperature during the isolation of highly pure organomonochlorosilane from the reaction solution. Moreover, the method accompanies the generation of sulfur dioxide as a by-product, but the by-product is a gaseous substance. Therefore, the by-product does not remain in the reaction vessel at all, can easily be discharged from the reaction system and accordingly, the post-treatment of the reactor is very easy. As a result, the organomonochlorosilane can be recovered from a constant volume of the reaction solution in an amount greater than those obtained according to the conventional methods (an improvement of the pot yield). The method can easily be handled and has high safety since the method does not require the use of dangerous reagents and does not accompany the formation of dangerous products and/or by-products.

DETAILED EXPLANATION OF THE INVENTION

If the substituents $R^1$ to $R^6$ bonded to the silicon atoms of the organodisiloxane which undergoes a reaction with thionyl chloride are monovalent hydrocarbon groups, they may be saturated or unsaturated groups. They may be noncyclic hydrocarbon groups or cyclic hydrocarbon groups. These monovalent hydrocarbon groups may be unsubstituted or substituted with substituents such as halogen atoms and/or cyano group. Specific examples of such organodisiloxanes are pentamethyl-t-butyl-disiloxane: $[(CH_3)_3C](CH_3)_2SiOSi(CH_3)_3$, 1,3-dimethyl-1,1,3,3-tetraphenyl-disiloxane: $(C_6H_5)_2(CH_3)SiOSi(CH_3)(C_6H_5)_2$, 1,1,3,3-tetramethyl-disiloxane: $(CH_3)_2HSiOSiH(CH_3)_2$, 1,3-di-(cyanoethyl)-1,1,3,3-tetramethyl-disiloxane: $[(CN)C_2H_4](CH_3)_2SiOSi(CH_3)_2[C_2H_4(CN)]$, 1,1,3,3-tetramethyl-1,3-diisopropyl-disiloxane: $[(CH_3)_2CH](CH_3)_2SiOSi(CH_3)_2[CH(CH_3)_2]$, 1,3-dicyclohexyl-1,1,3,3-tetramethyl-disiloxane: $(C_6H_{11})(CH_3)_2SiOSi(CH_3)_2(C_6H_{11})$, hexamethyl-disiloxane: $(CH_3)_3SiOSi(CH_3)_3$, 1,3-divinyl-1,1,3,3-tetramethyl-disiloxane: $(CH_2CH)(CH_3)_2SiOSi(CH_3)_2(CHCH_2)$ and 1,3-diallyl-1,1,3,3-tetramethyl-disiloxane: $(CH_2CHCH_2)(CH_3)_2SiOSi(CH_3)_2(CH_2CHCH_2)$. These compounds may be used alone or in any combination. Among these compounds, particularly preferred are, for instance, pentamethyl-t-butyl-disiloxane, hexamethyl-disiloxane and 1,3-divinyl-1,1,3,3-tetramethyl-disiloxane.

The substituents $R^7$ to $R^{10}$ of the ammonium salt represented by Formula: $R^7R^8R^9R^{10}NX$ used as the catalyst for the reaction may be the same monovalent hydrocarbon group defined above in connection with the substituents $R^1$ to $R^6$, provided that $R^{10}$ may be a hydrogen atom. The substituent X in the ammonium salt represents a monovalent anion such as a chloride ion, a bromide ion, a sulfate ion or a perchlorate ion. Specific examples of such ammonium salts include tertiary ammonium salts such as trimethylamine hydrochloride: $(CH_3)_3NHCl$, triethylamine hydrochloride: $(C_2H_5)_3NHCl$, tributylamine hydrochloride: $[CH_3(CH_2)_3]_3NHCl$, N,N-dimethyl-phenylamine hydrobromide: $(C_6H_5)(CH_3)_2NHBr$, N,N-diethyl-phenylamine hydrobromide: $(C_6H_5)(C_2H_5)NHBr$ and N-ethyl-diphenylamine hydrobromide: $(C_6H_5)_2(C_2H_5)NHBr$; and quaternary ammonium salts such as tetrabutylammonium chloride: $[CH_3(CH_2)_3]_4NCl$, tetrabutylammonium bromide:

[CH$_3$(CH$_2$)$_3$]$_4$NBr and tetramethylammonium sulfate: [(CH$_3$)$_4$N]$_2$SO$_4$. These ammonium salts may be used alone or in any combination.

The intended organomonochlorosilane can be obtained by reacting the foregoing organodisiloxane with thionyl chloride in the presence of the ammonium salt. The reaction scheme will be given below:

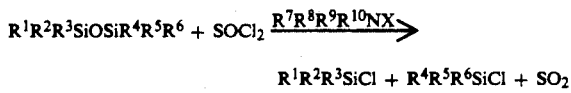

$$R^1R^2R^3SiOSiR^4R^5R^6 + SOCl_2 \xrightarrow{R^7R^8R^9R^{10}NX}$$

$$R^1R^2R^3SiCl + R^4R^5R^6SiCl + SO_2$$

Specific examples of the organomonochlorosilane obtained by the foregoing reaction are t-butyl-dimethyl-chlorosilane: [(CH$_3$)$_3$C](CH$_3$)$_2$SiCl, trimethyl-chlorosilane: (CH$_3$)$_3$SiCl, vinyl-dimethyl-chlorosilane: (CH$_2$CH)(CH$_3$)$_2$SiCl, allyl-dimethyl-chlorosilane: (CH$_2$CHCH$_2$)(CH$_3$)$_2$SiCl, ethynyl-dimethyl-chlorosilane: (HCC)(CH$_3$)$_2$SiCl, (cyanoethyl)-dimethyl-chlorosilane: [(CN)C$_2$H$_4$](CH$_3$)$_2$SiCl, methyl-diphenyl-chlorosilane: (C$_6$H$_5$)$_2$(CH$_3$)SiCl and diisopropyl-chlorosilane: [(CH$_3$)$_2$CH]$_2$HSiCl.

The reaction of the organodisiloxane with thionyl chloride is preferably carried out, for instance, in the following manner. An organodisiloxane and an ammonium salt as a catalyst are introduced into a reaction vessel and then thionyl chloride is dropwise added to the mixture with stirring. The amount of the ammonium salt to be charged in general ranges from 0.1 to 10 moles and preferably 2 to 7 moles per 100 moles of the organodisiloxane. The reaction temperature ranges from 0° to 200° C. and preferably 10° to 90° C. It is preferred that water be dropwise added to the reaction vessel along with thionyl chloride. An acid may be added to the reactor in combination with or in place of water. In any case, the reaction rate can be improved.

If water or an acid is introduced into the reaction vessel, a tertiary amine such as tributylamine can, in fact, be substituted for the ammonium salt. More specifically, if an acid is introduced into the reactor, the acid forms a tertiary ammonium salt through the reaction with a tertiary amine in the reactor and the resulting tertiary ammonium salt serves as a catalyst. On the other hand, if water is introduced into the reactor, it forms an acid through the reaction with thionyl chloride and the resulting acid undergoes a reaction with a tertiary amine in the reactor.

The organomonochlorosilane of high purity can be obtained by distilling the crude product prepared according to the foregoing method. Thus, according to the method of the present invention, organomonochlorosilanes of high purity can be obtained in a high yield by reacting organodisiloxanes with thionyl chloride. Sulfur dioxide is simultaneously formed during the reaction as a by-product. It is externally discharged from the reaction vessel and can be recovered using a scrubber (washing collector) which makes use of an alkali aqueous solution such as an aqueous sodium hydroxide solution.

The present invention will hereinafter be explained with reference to the following Examples, but the present invention is by no means limited to these specific Examples.

EXAMPLE 1

To a 200 ml volume reaction vessel equipped with a stirring machine, a reflux condenser, a dropping funnel and an inlet pipe for hydrogen chloride gas, there were added 51.1 g (0.25 mole) of pentamethyl-t-butyl-disiloxane and 4.16 g (0.015 mole) of tetrabutylammonium chloride and 41.6 g (0.35 mole) of thionyl chloride was charged in the dropping funnel.

The reaction system was stirred at room temperature while dropwise adding thionyl chloride through the dropping funnel. In this manner, pentamethyl-t-butyl-disiloxane was reacted with thionyl chloride while dropwise adding the latter and supplying hydrogen chloride gas to the reaction solution. After stirring the reaction solution over 4 hours, it was distilled at 125° C. to give 31.3 g (yield 83.2%) of t-butyldimethylchlorosilane and 21.4 g (yield 79.0%) of trimethylchlorosilane. There was not observed the formation of any viscous oily substance, the distillation temperature during the purification could substantially be decreased and the post-treatment of the reaction vessel was very easy.

EXAMPLE 2

To a 1.0 l volume reaction vessel equipped with a stirring machine, a reflux condenser, a dropping funnel and an inlet pipe for hydrogen chloride gas, there were added 204 g (1.0 mole) of pentamethyl-t-butyl-disiloxane and 9.25 g (0.050 mole) of tributylamine and 143 g (1.2 mole) of thionyl chloride was introduced into the dropping funnel. Pentamethyl-t-butyl-disiloxane was reacted with thionyl chloride at room temperature by dropwise adding thionyl chloride through the dropping funnel while supplying hydrogen chloride gas to the reaction solution. After stirring over 4 hours, the reaction solution was distilled at 125° C. to give 130 g (yield 86.4%) of t-butyldimethylchlorosilane and 87.0 g (yield 80.2%) of trimethylchlorosilane. There was not observed the formation of any viscous oily substance, the distillation temperature during the purification could substantially be decreased and the post-treatment of the reaction vessel was very easy.

EXAMPLE 3

The same procedures used in Example 2 were repeated except that a 500 ml volume reaction vessel was substituted for the 1.0 l volume reaction vessel, that 186 g of 1,3-divinyl-1,1,3,3-tetramethyl-disiloxane was substituted for 204 g of the pentamethyl-t-butyl-disiloxane and that the distillation temperature was set at 85° C. to give 198 g (yield 82.0%) of dimethylvinylchlorosilane. There was not observed the formation of any viscous oily substance, the distillation temperature during the purification could substantially be decreased and the post-treatment of the reaction vessel was very easy.

What is claimed is:

1. A method for preparing an organomonochlorosilane comprising the step of reacting an organodisiloxane represented by the general formula (I):

$$R^1R^2R^3SiOSiR^4R^5R^6 \qquad (I)$$

with thionyl chloride in the presence of an ammonium salt represented by the general formula (II):

$$R^7R^8R^9R^{10}NX \qquad (II)$$

wherein $R^1$ to $R^6$ and $R^{10}$ may be the same or different and each represents a monovalent hydrocarbon group or a hydrogen atom; $R^7$ to $R^9$ may be the same or different and each represents a monovalent hydrocarbon group; and x represents a monovalent anion.

2. The method of claim 1 wherein the organodisiloxane represented by the general formula (I) is pentamethyl-t-butyl-disiloxane: $[(CH_3)_3C](CH_3)_2SiOSi(CH_3)_3$.

3. The method of claim 1 or 2 wherein the amount of the ammonium salt represented by the general formula (II) ranges from 0.1 to 10 moles per 100 moles of the organodisiloxane represented by the general formula (I).

4. The method of claim 1 wherein a tertiary amine and water and/or an acid are introduced into a reaction vessel in which the organodisiloxane is reacted with thionyl chloride to form the ammonium salt represented by the general formula (II) in situ.

5. The method of claim 2 wherein a tertiary amine and water and/or an acid are introduced into a reaction vessel in which the organodisiloxane is reacted with thionyl chloride to form the ammonium salt represented by the general formula (II) in situ.

6. The method of claim 3 wherein a tertiary amine and water and/or an acid are introduced into a reaction vessel in which the organodisiloxane is reacted with thionyl chloride to form the ammonium salt represented by the general formula (II) in situ.

* * * * *